United States Patent [19]

Bertocchio et al.

[11] 4,383,929
[45] May 17, 1983

[54] FLUORINATED SULPHOBETAINES AND COMPOSITIONS CONTAINING THE SAME

[75] Inventors: René Bertocchio, Vourles par Vernaison; Louis Foulletier, Oullins; André Lantz, Vernaison, all of France

[73] Assignee: Produits Chimiques Ugine Kuhlmann, Courbevoie, France

[21] Appl. No.: 133,477

[22] Filed: Mar. 24, 1980

[30] Foreign Application Priority Data

Apr. 6, 1979 [FR] France ................................. 79 08749

[51] Int. Cl.³ .......................... A62D 1/00; B01F 17/24; B01F 17/26; C07C 143/76
[52] U.S. Cl. .................................. 252/8.05; 252/355; 252/DIG. 7; 260/501.12
[58] Field of Search ................ 252/8.05, 355, DIG. 7; 260/501.12, 501.13

[56] References Cited

U.S. PATENT DOCUMENTS

| | | | |
|---|---|---|---|
| 3,258,423 | 6/1966 | Tuve et al. ............................. | 252/3 |
| 3,562,156 | 2/1971 | Francen ................................ | 252/8.05 |
| 3,941,705 | 3/1976 | Foulletier et al. ..................... | 252/8.05 |
| 3,950,417 | 4/1976 | Verdicchio et al. ................... | 252/DIG. 7 |
| 4,099,574 | 7/1978 | Cooper et al. ........................ | 252/8.05 X |

FOREIGN PATENT DOCUMENTS

| | | |
|---|---|---|
| 2084888 | 12/1971 | France . |
| 2086904 | 12/1971 | France . |
| 2088594 | 1/1972 | France . |
| 2088699 | 1/1972 | France . |
| 2088941 | 1/1972 | France . |
| 2122918 | 9/1972 | France . |
| 2185668 | 1/1974 | France . |
| 2308674 | 11/1976 | France . |
| 2373551 | 7/1978 | France . |

OTHER PUBLICATIONS

Barnhurst: "Dipolar Ions Related to Taurine", J. Org. Chem. 1961, 26, pp. 4520–4522.
Parris et al.: Soap–Based Detergent Formulations: XII. Alternate Syntheses of Surface Active Sulfobetaines", J. Of Amer. Oil Chem. Soc. 1976, 53, pp. 60–63.
Parris et al.: Soap–Based Detergent Formulation: XXIV. Sulfobetaine Derivatives of Fatty Amides", J. of Amer. Oil Chem. Soc. 1977, 54, pp. 294–296.

Primary Examiner—Richard D. Lovering
Attorney, Agent, or Firm—Sigalos & Levine

[57] ABSTRACT

A fluorinated sulphobetaine compound of the general formula

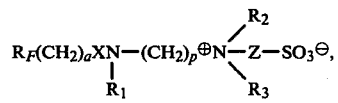

wherein $R_F$ represents a straight-chained or branched perfluorinated aliphatic chain $C_nF_{2n+1}$ (n being an integer between 1 and 20), a is an integer between 0 and 10, X is CO or $SO_2$, p is an integer between 0 and 10, $R_1$ is a hydrogen atom or an alkyl group containing 1 to 6 carbon atoms, $R_2$ and $R_3$ are each alkyl radicals containing 1 to 6 carbon atoms, and Z is a bivalent organic group; and fire extinguishing compositions comprising such fluorinated sulphobetaine compounds.

6 Claims, No Drawings

FLUORINATED SULPHOBETAINES AND COMPOSITIONS CONTAINING THE SAME

BACKGROUND OF THE INVENTION

The present invention relates to a new class of ampholytic fluorinated surface-active agents, characterized in that they contain in the same molecule an aliphatic perfluorinated radical, a quaternary ammonium group and an anionic sulphonic group chemically bonded to the quaternary ammonium group by a bivalent group, which are especially useful as fire extinguishing agents.

Numerous amphoteric fluorinated surfactants are known. For example, the following compound is described in U.S. Pat. Nos. 3,258,423 and 3,562,156:

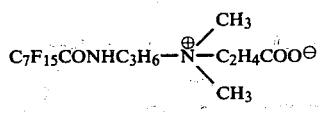

French Pat. Nos. 2,088,699, 2,088,941 and 2,084,888 describe the products of the following formulas:

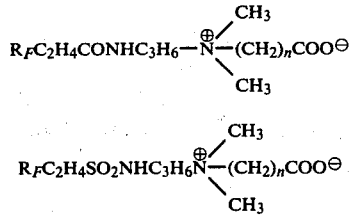

These amphylotic products have been used for numerous applications in very varied fields, but particularly in the field of fire extinguishing agents (cf. for example Nos. 2,185,668 and 2,308,674).

However, these ampholytic surfactants are all carboxylic ampholytes, i.e., products wherein the anionic group is the carboxyl anion $CO_2^-$. Other ampholytic fluorinated surfactants have been described. Thus, French Pat. No. 2,373,551 claims compounds wherein the anionic group is the phosphorus anion and French Pat. No. 2,122,918 claims products wherein the anion is the sulphonic group $SO_3^-$, such as, for example:

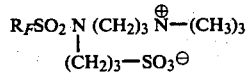

The sulphobetaines corresponding to this latter publication are characterized in that the quaternary ammonium and sulphonic groups contained in their molecule are both in the end position and are regarded as non-linear sulphobetaines.

SUMMARY OF THE INVENTION

The present invention relates to a new class of ampholytic fluorinated surface-active compounds which can be regarded as linear amphoteric surfactants, characterized in that they have no quaternary ammonium in the end position and contain in the same molecule an aliphatic perfluorinated radical, a quaternary ammonium group and an anionic sulphonic group chemically bonded to the quaternary ammonium group by a bivalent group; which compounds are especially useful as fire extinguishing agents.

More specifically, the present invention relates to fluorinated sulphobetaines having the general formula:

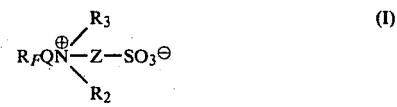

wherein $R_F$ represents a straight-chained or branched aliphatic perfluorinated chain $C_nF_{2n+1}$, n is an integer between 1 and 20, Q and Z each represent bivalent organic bonding groups, and $R_2$ and $R_3$ are each alkyl radicals generally containing 1 to 6 carbon atoms.

Especially preferred and particularly effective compounds corresponding to this general formula are represented by the general formula:

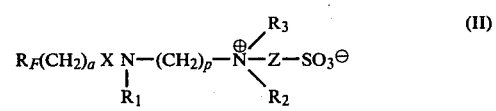

wherein $R_F$, $R_2$, $R_3$, and Z have the same meanings as before and a is an integer between 0 and 10, X is a CO or $SO_2$ radical, $R_1$ is a hydrogen atom or an alkyl group containing 1 to 6 carbon atoms, and p is an integer between 0 and 10.

In this same formula, Z again represents a bivalent organic bonding, in particular, $(CH_2)_q$ wherein q is an integer between 1 and 10, preferably between 1 and 3. However, Z may also represent a more complex group, in particular, polymethylene radicals substituted either by alkyl groups or by functional groups such as OH or COOH.

The invention also relates to extinguishing compositions comprising such fluorinated sulphobetaines.

DETAILED DESCRIPTION

The invention will be described in connection with the sulphobetaines of formula (II) above as will the processes for preparing the instant novel compounds which are different from those required for the preparation of the non-linear sulphobetaines described in French Pat. No. 2,122,918 mentioned above.

Among the compounds which are representative of the invention and formula (II) there are:

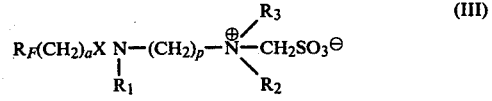

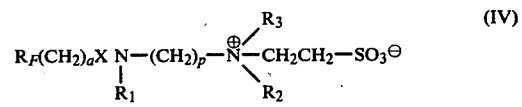

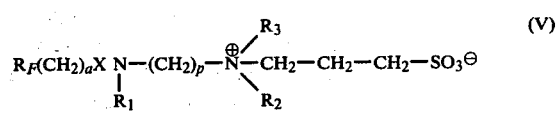

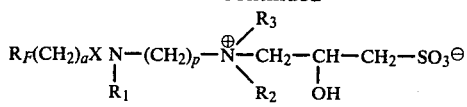 (VI)

The sulphobetaines according to formulas (II), (III), (IV), (V), and (VI), can be obtained by quaternization of amines of formula:

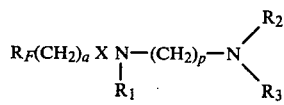 (VII)

wherein $R_F$, X, $R_1$, $R_2$, $R_3$, a and p have the same meanings as first set forth above.

The amines (VII), namely:

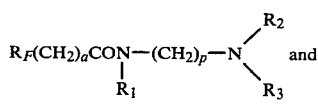 and

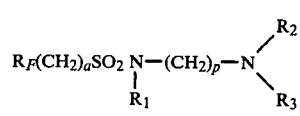

are already known and can be prepared, for example, by the methods set forth in French Pat. Nos. 2,086,904 and 2,088,594; in particular, by reacting diamines

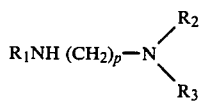

with sulphonic acid chlorides $R_F(CH_2)_aSO_2Cl$, or carboxylic acid chlorides $R_F(CH_2)_aCOCl$.

By reason of ready availability, amines of formula (VII) are preferred wherein a=0 or 2, $R_1$ is H or methyl, $R_2$ and $R_3$ are each methyl, and p is 2 or 3; and more particularly the following products:

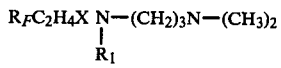

wherein X represents CO or $SO_2$ and $R_1$ represents hydrogen or a methyl radical.

The sulphobetaines can be obtained from amines of formula (VII) by reacting with salts of halogenosulphonic acids or with sultones. Other quaternization processes can also be used, some of which are indicated hereinafter. The sulphobetaines of formula (III) wherein Z=—$CH_2$— can thus be obtained by reacting the amine with a salt of chloro- or bromomethanesulphonic acid.

The sulphobetaines of formula (IV), i.e. the derivatives of general formula (II) with Z=—$CH_2$—$CH_2$— can be obtained by reacting the amine (VII) with a salt of 2-chloro- or 2-bromo-ethanesulphonic acid, for example, according to the following reaction:

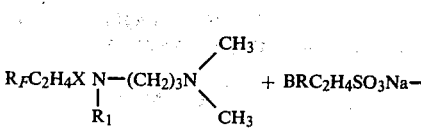

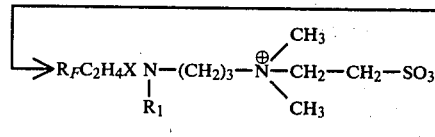

This same product can also be obtained by a method (J. Org.) Chem. 1961, 26, 4521) consisting in quaternizing the amine with dibromoethane and reacting the resulting monosalt with sodium sulphite:

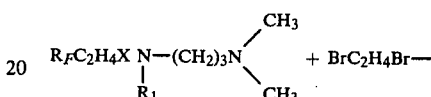

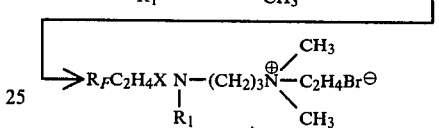

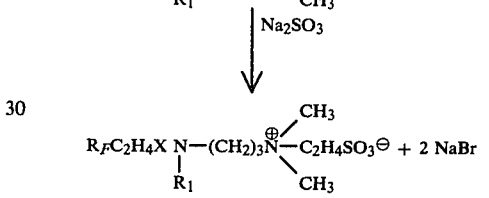

The betaines of formula (V) can be obtained according to known methods, by reacting the amine (VII) either with sultone propane

or with a salt of 3-chloropropanesulphonic acid. The same products can also be obtained according to a method described in J. of American Oil Chem. Soc. 1977, 54, p. 294, consisting of quaternizing the amine with allyl chloride and reacting this salt with sodium bisulphite.

The betaines of formula (VI) can be prepared according to a method described in J. of American Oil Chem. Soc. 1976, 53, 60 and represented, in the case of the products according to the invention, by the following reactions:

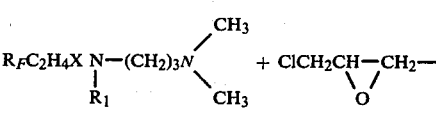

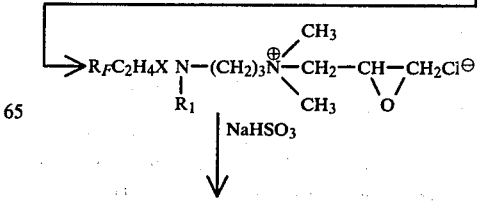

-continued $$R_FC_2H_4X\underset{R_1}{N}-(CH_2)_3\overset{\oplus}{N}\underset{CH_3}{\overset{CH_3}{\diagup}}-CH_2-\underset{OH}{CH}-CH_2SO_3^{\ominus} + NaCl$$

The order of these reactions may also be reversed, by first reacting the epichlorohydrin with sodium bisulphite and reacting the resulting product, namely $$ClCH_2\underset{OH}{CH}-CH_2SO_3Na,$$

with the amine.

The sulphobetaines of the invention are excellent surface-agents. However, as these products have low solubility in water (solubility generally less than 0.1% at ambient temperature), it may be advantageous, for some applications, to use these sulphobetaines in admixture with other surfactants, which may or may not be fluorinated; in particular with non-ionic surfactants, which can increase the solubility of the fluorinated products. These products also have the particular feature of being more soluble, even in the presence of co-surfactants, in aqueous saline solutions than in fresh water. In order to obtain solutions with a relatively high concentration of the products according to the invention, it is sometimes desirable to add a certain quantity of light alcohols, such as glycols or glycol ethers and the like.

These surface-active properties are illustrated by the following Table I, which gives the surface tension values at 20° C. for some sulphobetaines of the invention, in a concentration of 0.1%, in the presence of 0.3% of a non-fluorinated non-ionic surfactant, for example, a 10 O E ethoxylated octylphenol sold under the trademark Triton X 100 by ROHM & HAAS, in artificial sea water corresponding to the following composition, by weight:

| | | |
|---|---|---|
| 1.1% | $MgCl_2$, | 6 $H_2O$ |
| 0.16% | $CaCl_2$, | 2 $H_2O$ |
| 0.4% | $Na_2SO_4$ | |
| 2.5% | NaCl | |
| 95.84% distilled water | | |

The surface tension of this solution containing only 0.3% of Triton X 100 without any fluorinated products is 26 dynes/cm at 20° C.

TABLE I

| Sulphobetaine | Surface Tension Value |
|---|---|
| $C_6F_{13}C_2H_4SO_2NH-C_3H_6-\overset{\oplus}{N}(CH_3)_2-CH_2-CH_2-SO_3^{\ominus}$ | 15.3 |
| $C_6F_{13}C_2H_4SO_2NH-C_3H_6-\overset{\oplus}{N}(CH_3)_2-CH_2-CH_2-CH_2-SO_3^{\ominus}$ | 14.5 |
| $C_6F_{13}C_2H_4SO_2NH-C_3H_6-\overset{\oplus}{N}(CH_3)_2-CH_2-CH(OH)CH_2-SO_3^{\ominus}$ | 14.5 |
| $C_6F_{13}C_2H_4SO_2N(CH_3)-C_3H_6-\overset{\oplus}{N}(CH_3)_2-CH_2-CH_2-CH_2-SO_3^{\ominus}$ | 16.8 |
| $R^*_FC_2H_4SO_2NH-C_3H_6-\overset{\oplus}{N}(CH_3)_2-CH_2-CH_2-CH_2-SO_3^{\ominus}$ | 13.8 |

$R^*_F$ = Mixture of $C_6F_{13}$ to $C_{18}F_{37}$ homologues as specified in Example 5

The good surface-active properties of sulphobetaines can also be demonstrated by their ability to form a film on the surface of a hydrocarbon when an aqueous solution of surfactants is placed on the hydrocarbon. It is known, from U.S. Pat. Nos. 3,258,423 and 3,562,156, that aqueous solutions of surfactants which form a film on the surface of hydrocarbons can be used as fire extinguishing agents. This property can be characterized by measuring the rate of spreading. This rate can be determined as follows:

A glass dish 120 mm in diameter is half-filled with cyclohexane. 0.1 ml of the surfactant solution is placed in the centre of the pool of hydrocarbon. The difference in reflecting power makes it possible to follow the progression of the fluorinated film and thus measures the time taken to cover the entire surface. This spreading test can be carried out with solutions of surfactants at different concentrations in fresh water and sea water.

A certain number of sulphobetaines were subjected to this spreading test on cyclohexane, in admixture with a non-fluorinated non-ionic surfactant, namely Triton X 100.

First, the following solutions were prepared:

(A) $C_6F_{13}C_2H_4SO_2NH(CH_2)_3\overset{\oplus}{N}(CH_3)_2-CH_2-\underset{OH}{CH}-CH_2-SO_3^{\ominus}$  5.5 g Triton X 100  14.4 g
Ethanol  36 g
Water  74.1 g (B) $C_6F_{13}C_2H_4SO_2NH(CH_2)_3\overset{\oplus}{N}(CH_3)_2-CH_2-CH_2-CH_2-SO_3^{\ominus}$  5.35 g

|  |  |  |
|---|---|---|
| Triton X 100 |  | 14.4 g |
| Ethanol |  | 36 g |
| Water |  | 74.25 g |
| (C) | $C_6F_{13}C_2H_4SO_2NH(CH_2)_3\overset{\oplus}{N}(CH_3)_2\text{—}CH_2\text{—}CH_2\text{—}SO_3^{\ominus}$ | 5.20 g |
| Triton X 100 |  | 14.4 g |
| Ethanol |  | 36 g |
| Water |  | 74.4 g |
| (D) | $C_8F_{17}C_2H_4CONH(CH_2)_3\overset{\oplus}{N}(CH_3)_2\text{—}CH_2\text{—}CH_2\text{—}CH_2SO_3^{\ominus}$ | 4.5 g |
| Triton X 100 |  | 14.4 g |
| Ethanol |  | 6 g |
| Water |  | 75.10 g |

Solutions A, B, C, and D were then diluted with fresh water and with artificial sea water so as to have a fluorine concentration of 520 mg per liter, and the spreading rates of these solutions were determined. The following results were obtained:

| | Spreading Rate Solution corresponding to 520 mg/liter of fluorine in | |
|---|---|---|
| | Fresh water | Sea water |
| Solution A |  | 2.5 seconds |
| Solution B | 3 seconds | 2 seconds |
| Solution C | 8.5 seconds | 3.5 seconds |
| Solution D | 7 seconds | 15 seconds |

Solution A in fresh water is not fully soluble at the concentration used for these tests and the spreading rate was not measured. It is still possible to obtain a film with smaller quantities of fluorinated product. Thus, products B and D, diluted in fresh water to 340 mg/liter of fluorine, have spreading rates of 6.5 seconds. The spreading results are generally better in a saline medium than in fresh water. Thus, at a concentration of 170 mg of fluorine per liter, product B spreads in 18.5 seconds in a sea water medium and gives only a partial spreading in a fresh water medium. The same is true of product C, which spreads in 9 seconds at 340 mg/liter of fluorine in a sea water medium and spreads only partially in fresh water.

The invention will be further described in connection with the following examples, which are given for purposes of illustration only.

EXAMPLE 1

13 g of sultone propane dissolved in 30 ml of chloroform are added to a solution of 57.6 g of $C_8F_{17}C_2H_4CONHC_3H_6N(CH_3)_2$ in 85 ml of chloroform, with stirring and maintaining the temperature at 20° C. The introduction of the sultone propane is carried out within 30 minutes, then the reaction mixture is stirred for 4 hours. A white precipitate forms during this reaction. By filtering the reaction mixture after cooling it in ice, washing the precipitate with 50 ml of chloroform, and drying in vacuo, 62 g of a product are obtained, which melts, with decomposition, at 155° C. By IR and NMR examination, it is identified as:

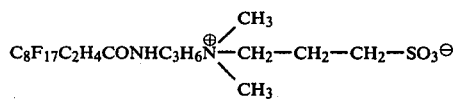

The yield in this operation is 89%.

An aqueous solution containing 1,000 ppm of this product in the presence of 3,000 ppm of Triton X 100 has a surface tension of 15.3 dynes/cm at 20° C. At the same temperature, an aqueous solution of 3,000 ppm of Triton X 100 has a surface tension of 26 dynes/cm.

EXAMPLE 2

51.2 g of

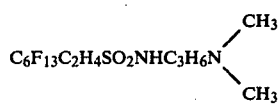

and 100 ml of chloroform are placed in a 250 ml reactor. After complete dissolution, 13.4 g of sultone propane are added in one hour at ambient temperature. The mixture is stirred for 12 hours, then the solid product formed is filtered, washed with 50 ml of chloroform and dried in vacuo.

58 g of a white solid product are thus obtained, melting, with decomposition, at 200°-220° C., identified as being:

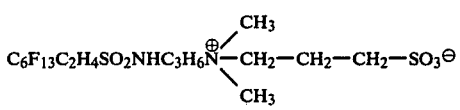

EXAMPLE 3

51.2 g of

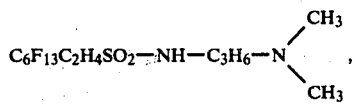

100 ml of 95% ethanol and 22.1 g of Br—C₂H₄SO₃Na are placed in a 250 ml reactor and the mixture is refluxed, with stirring. After 24 hours, there are still 6.5% of unconverted amine. Refluxing is continued for 8 hours, to give a content of unconverted starting amine of 1.5%. The mixture is then filtered hot and, by evaporation of the filtrate, 70 g of a white powdery product are obtained, identified as being

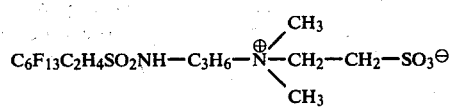

This product contains 13.4% of sodium bromide which can be eliminated by washing with water, but the crude product is suitable for most applications.

EXAMPLE 4

Using the method of Example 2, 52.6 g of

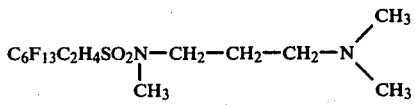

are used, and 62 g of

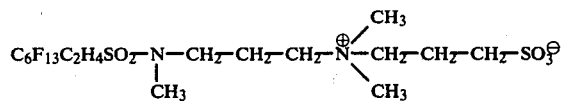

are obtained. This product is in the form of a white powder, which decomposes above 200°–220° C.

EXAMPLE 5

Using the method of Example 2, 56 g of

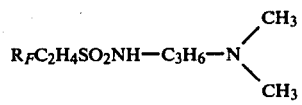

are used.

This product is a mixture of the different homologues, containing:

2% of product with $R_F=C_4F_9$
50% of product with $R_F=C_6F_{13}$
28% of product with $R_F=C_8F_{17}$
12% of product with $R_F=C_{10}F_{21}$
5% of product with $R_F=C_{12}F_{25}$
2% of product with $R_F=C_{14}F_{29}$
0.6% of product with $R_F=C_{16}F_{33}$
0.2% of product with $R_F=C_{18}F_{37}$ After reacting with the sultone propane, filtration and drying, 60 g of a powdered product are obtained, which is identified by IR and NMR examination as being:

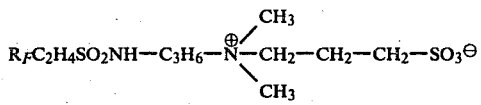

EXAMPLE 6

A solution containing 64 g of NaHSO₃, 25 g of Na₂SO₃ and 150 g of water is added in one hour to a 250 ml reactor containing 50 g of epichlorohydrin,

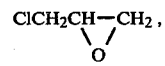

and the temperature is kept at 20° C. by cooling. The added solution is obtained by dissolving sodium sulphite in a 30% sodium bisulphite solution. After the solution is added, the mixture is stirred for another two hours at ambient temperature, then 95 g of a white crystalline solid corresponding to ClCH₂CH(OH)CH₂SO₃Na are obtained by filtration and drying in vacuo.

Then 21.6 g of this product are placed in a reactor containing 51.2 g of

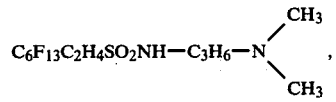

100 ml of ethanol and 20 ml of water.

The mixture is refluxed to boiling point with stirring and the disappearance of the amine is monitored by acidimetric measurement. After 15 hours heating there are still 15% of unconverted amine, after 22 hours 6.6%, and after 34 hours 3%. The operation is then stopped and, by evaporation in vacuo, 70 g of a white powdery product corresponding to the following formula is obtained:

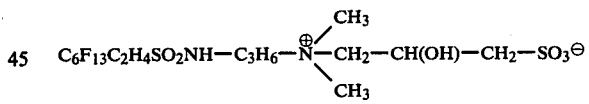

The crude product obtained according to this process contains 8.2% of sodium chloride. It can be purified by dissolving it in absolute ethanol, filtering the sodium chloride and evaporating the ethanol to dryness.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A linear fluorinated sulphobetaine compound having the formula:

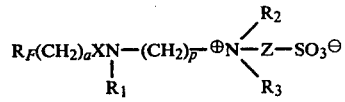

wherein $R_F$ is a straight-chained or branched aliphatic perfluorinated chain $C_nF_{2n+1}$, n being an integer from 1 to 20, a is an integer from 0 to 10, X is a CO or $SO_2$ radical, p is an integer from 0 to 10, $R_1$ is a hydrogen atom or an alkyl radical containing 1 to 6 carbon atoms, $R_2$ and $R_3$ are each alkyl radicals containing 1 to 6 carbon atoms, and Z is a lower alkylene radical having the formula $(CH_2)_q$ wherein q is an integer from 1 to 10 or a polymethylene radical substituted either by an alkyl group or by the functional group OH or COOH.

2. The compound of claim 1, wherein a is equal to 2, p is equal to 3, $R_1$ is a hydrogen or methyl radical, and $R_2$ and $R_3$ are each methyl radicals.

3. The compound of claims 1 or 2, wherein Z is selected from a lower alkylene radical having the formula $-(CH_2)_q-$ wherein q is an integer from 1 to 3.

4. A fluorinated sulphobetaine compound having the formula:

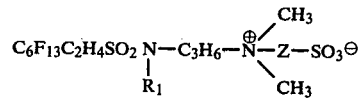

wherein $R_1$ is selected from a hydrogen atom or a methyl radical and Z is selected from $-CH_2-CH_2-$, $-CH_2-CH_2-CH_2-$, or $-CH_2-CH(OH)-CH_2-$.

5. A fire extinguishing composition comprising a solution of a compound of claims 1, 2, or 4.

6. A fire extinguishing composition comprising an aqueous or aqueous saline solution of a fluorinated sulphobetaine compound of claims 1, 2, or 4 and a non-fluorinated non-ionic surfactant, said fluorinated sulphobetaine compound being present in said solution in an amount sufficient to obtain a good spreading rate of the composition on the surface of hydrocarbons.

* * * * *